(12) United States Patent
Willhite et al.

(10) Patent No.: US 11,717,342 B2
(45) Date of Patent: Aug. 8, 2023

(54) MEDICAL DEVICE

(71) Applicant: Gyrus ACMI, Inc., Southborough, MA (US)

(72) Inventors: Joel A. Willhite, Memphis, TN (US); Ahmad Alsaffar, Bartlett, TN (US); Kevin C. Edwards, Olive Branch, MS (US)

(73) Assignee: Gyrus ACMI, Inc., Westborough, MA (US)

( * ) Notice: Subject to any disclaimer, the term of this patent is extended or adjusted under 35 U.S.C. 154(b) by 420 days.

(21) Appl. No.: 16/365,735

(22) Filed: Apr. 11, 2019

(65) Prior Publication Data

US 2020/0323582 A1 Oct. 15, 2020

(51) Int. Cl.
*A61B 18/14* (2006.01)
*A61B 17/3207* (2006.01)
*A61B 18/00* (2006.01)

(52) U.S. Cl.
CPC .. *A61B 18/1485* (2013.01); *A61B 17/320783* (2013.01); *A61B 2018/00327* (2013.01);
(Continued)

(58) Field of Classification Search
CPC ........ A61B 18/1485; A61B 17/320783; A61B 2018/00327; A61B 2018/00601; A61B 2018/00607; A61B 2018/142; A61B 18/1482; A61B 2018/1475; A61B 2018/00255; A61B 2018/00202; A61B 2018/126; A61B 2218/002;
(Continued)

(56) References Cited

U.S. PATENT DOCUMENTS 3,054,464 A 9/1962 Ondeck
3,201,670 A 8/1965 Myers
(Continued)

FOREIGN PATENT DOCUMENTS

EP 3698746 A1 8/2020
EP 3721824 A1 10/2020
(Continued)

OTHER PUBLICATIONS

European Search Report, EP Application No. 20 168 120.2, dated Jul. 28, 2020, 9 pages.
(Continued)

*Primary Examiner* — Khadijeh A Vahdat
*Assistant Examiner* — Mystee Nguyen Delgado
(74) *Attorney, Agent, or Firm* — Schwegman Lundberg & Woessner, P.A.

(57) ABSTRACT

Provided is a medical device comprising an inner tubular member, an outer tubular member having a distal end and an open window disposed at the distal end, a first electrode and/or a second electrode disposed at the distal end of the outer tubular member, and a cannulated plunger or armature or shaft configured to drive the inner tubular member to cut tissue in cooperation with the open window of the outer tubular member. The first electrode and the second electrode may be configured to provide RF energy needed for a surgical operation and may be configured to be substantially symmetrical or asymmetrical along a longitudinal axis of the outer tubular member.

19 Claims, 9 Drawing Sheets

(52) U.S. Cl.
CPC .............. *A61B 2018/00601* (2013.01); *A61B 2018/00607* (2013.01); *A61B 2018/142* (2013.01)

(58) Field of Classification Search
CPC .... A61B 2218/007; A61B 2018/00577; A61B 2018/1405; A61B 2018/1412; A61B 18/148; A61B 18/149; A61B 2018/1497; A61B 2218/001; A61B 2018/1467; A61B 2018/00071; A61B 2018/162; A61B 17/320016; A61B 17/32002; A61B 2017/320028; A61B 2017/320024; A61B 17/24; A61B 2017/246; A61B 2018/00208; A61B 2018/00589
See application file for complete search history.

(56) References Cited

U.S. PATENT DOCUMENTS

| | | | |
|---|---|---|---|
| 5,364,395 A | 11/1994 | West, Jr. et al. | |
| 6,190,385 B1 | 2/2001 | Tom et al. | |
| 6,193,715 B1 | 2/2001 | Wrublewski et al. | |
| 6,258,111 B1* | 7/2001 | Ross | A61F 9/00763 606/171 |
| 6,293,957 B1 | 9/2001 | Peters et al. | |
| 7,150,747 B1* | 12/2006 | McDonald | A61B 18/148 606/49 |
| 7,174,220 B1 | 2/2007 | Chitre et al. | |
| 7,226,459 B2 | 6/2007 | Cesarini et al. | |
| 7,510,563 B2 | 3/2009 | Cesarini et al. | |
| 7,666,200 B2 | 2/2010 | Heisler | |
| 7,669,209 B2 | 2/2010 | Inohara et al. | |
| 7,669,309 B2 | 3/2010 | Johnson et al. | |
| 8,286,899 B2 | 10/2012 | Schowalter et al. | |
| 9,078,664 B2 | 7/2015 | Palmer et al. | |
| 9,446,229 B2 | 9/2016 | Omar-pasha | |
| 9,895,191 B2 | 2/2018 | Conley et al. | |
| 9,949,792 B2 | 4/2018 | Paul et al. | |
| 10,159,523 B2 | 12/2018 | Sartor et al. | |
| 10,188,456 B2* | 1/2019 | Prisco | A61B 18/1485 |
| 10,342,572 B2* | 7/2019 | Govari | A61F 9/00763 |
| 10,582,966 B2* | 3/2020 | Orczy-Timko | A61B 17/32 |
| 2006/0200123 A1* | 9/2006 | Ryan | A61B 18/148 606/48 |
| 2007/0250055 A1 | 10/2007 | Johnson et al. | |
| 2008/0125754 A1 | 5/2008 | Beer et al. | |
| 2008/0208233 A1 | 8/2008 | Barnes | |
| 2009/0012512 A1 | 1/2009 | Utley et al. | |
| 2010/0049191 A1 | 2/2010 | Habib et al. | |
| 2013/0331833 A1* | 12/2013 | Bloom | A61B 17/32002 606/33 |
| 2013/0345704 A1* | 12/2013 | Palmer | A61B 18/148 606/41 |
| 2014/0100567 A1* | 4/2014 | Edwards | A61B 17/32002 606/45 |
| 2015/0173825 A1 | 6/2015 | Bloom | |
| 2015/0327880 A1* | 11/2015 | Wasicek | A61B 17/32002 606/115 |
| 2015/0351826 A1 | 12/2015 | Kroeber et al. | |
| 2016/0235474 A1* | 8/2016 | Prisco | A61B 17/32002 |
| 2016/0361084 A1* | 12/2016 | Weisenburgh, II | A61B 18/1482 |
| 2017/0049514 A1 | 2/2017 | Cosman | |
| 2017/0143406 A1 | 5/2017 | Bloom | |
| 2017/0215955 A1 | 8/2017 | Hancock et al. | |
| 2017/0303986 A1 | 10/2017 | Hancock et al. | |
| 2017/0360497 A1 | 12/2017 | Hancock et al. | |
| 2018/0116711 A1 | 5/2018 | Suh | |
| 2019/0059983 A1 | 2/2019 | Germain et al. | |
| 2019/0231378 A1* | 8/2019 | Church | A61B 17/32002 |
| 2019/0321063 A1* | 10/2019 | Germain | A61B 18/1206 |
| 2020/0268435 A1 | 8/2020 | Alsaffar et al. | |

FOREIGN PATENT DOCUMENTS

| | | |
|---|---|---|
| JP | H08155031 A | 6/1996 |
| JP | 2014534874 A | 12/2014 |
| JP | 2015519147 A | 7/2015 |
| JP | 2017531514 A | 10/2017 |
| JP | 2018504983 A | 2/2018 |
| JP | 2020131042 A | 8/2020 |
| WO | WO-0033753 A1 | 6/2000 |
| WO | WO-0056238 A1 | 9/2000 |
| WO | WO-2008153357 A2 | 12/2008 |
| WO | WO-2014055131 A1 | 4/2014 |
| WO | 2015061643 A2 | 4/2015 |
| WO | WO-2015116692 A1 | 8/2015 |
| WO | WO-2016059228 A2 | 4/2016 |
| WO | WO-2016132340 A1 | 8/2016 |
| WO | WO-2016134156 A1 | 8/2016 |
| WO | WO-2017103209 A1 | 6/2017 |
| WO | WO-2019034710 A1 | 2/2019 |

OTHER PUBLICATIONS

"European Application Serial No. 20168120.2, Communication Pursuant to Article 94(3) EPC dated Jul. 26, 2021", 5 pgs.

"European Application Serial No. 20168120.2, Response filed Apr. 12, 2021 to Extended European Search Report dated Jul. 28, 2020", 8 pgs.

"Japanese Application Serial No. 2020-071135, Notification of Reasons for Refusal dated May 24, 2021", w/ English Translation, 11 pgs.

"THUNDERBEAT Generators". Retrieved Jan. 25, 2018, from http://medical.olympusamerica.com/products/thunderbeat-generators-esg-400-usg-400, 2 pages.

"Disposable Tonsil Adenoid Debrider". Retrieved Jan. 25, 2018, from http://medical.olympusamerica.com/products/debrider/dtad-70138400, 1 page.

"PolypVac". Retrieved Jul. 20, 2017, from https://zc1.campaign-view.com/ua/viewinbrowser?od=11287eca5dbc3b&rd=119f933bb603779b&sd=119f933bb6033495&n=11699e4beebbffe&mrd=119f933bb6033487&m=1, 2015, 2 pages.

"Straightshot M5 Microdebrider". Retrieved Jan. 25, 2018, from http://www.medtronic.com/for-healthcare-professionals/business-unit-landing-Page/straightshot-m5-30k-burs/index.htm, 1 page.

"Straightshot M4 Microdebrider". Retrieved Jan. 25, 2018, from ¬¬http://www.medtronic.com/us-en/healthcare-professionals/products/ear-nose-throat/powered-ent-instruments/powered-ent-instruments/handpieces-accessories.html, 1 page.

"Multidebrider Diego Elite". Retrieved Jan. 25, 2018, from ¬¬-http://medical.olympusamerica.com/products/debrider/diego%C2%AE-elite, 2 pages.

"Hightlights 2017 Otorhinolaryngology". Edition Jan. 2017. Retrieved Jan. 25, 2018, from https://www.karlstorz.com/cps/rde/xbcr/karlstorz_assets/ASSETS/3482434.pdf, 20 pages.

"ConMed". Retrieved Jan. 25, 2018, from http://www.conmed.com/en/products/orthopedics/ablation/bipolar-ablation/edge-bipolar-arthroscopic-rf-system, 2 pages.

"Smith & Nephew". Retrieved Jan. 25, 2018, from http://www.smith-nephew.com/professional/products/all-products/dyonics-power-ii-control-system/, 2 pages.

"ESSx Microdebrider". 2007. Retrieved Jan. 25, 2018, from https://nse.stryker.com/wp-content/uploads/2016/09/ESSx-Microdebrider-brochure.pdf, 2 pages.

"U.S. Appl. No. 16/282,760, Non Final Office Action dated Nov. 12, 2021", 17 pgs.

"European Application Serial No. 20158849.8, Extended European Search Report dated Jul. 6, 2020", 11 pgs.

"European Application Serial No. 20158849.8, Response filed Feb. 24, 2021 to Extended European Search Report dated Jul. 6, 2020", 11 pgs.

"Japanese Application Serial No. 2020-028554, Notification of Reasons for Rejection dated Mar. 22, 2021", w/ English Translation, 9 pgs.

(56) References Cited

OTHER PUBLICATIONS

"Japanese Application Serial No. 2020-028554, Response filed Jun. 21, 2021 to Notification of Reasons for Rejection dated Mar. 22, 2021", w/ English Claims, 10 pgs.

"Japanese Application Serial No. 2020-071135, Final Notification of Reasons for Refusal dated Nov. 22, 2021", w/ English Translation, 5 pgs.

"Japanese Application Serial No. 2020-071135, Response filed Aug. 13, 2021 to Notification of Reasons for Refusal dated May 24, 2021", w/o English Claims, 5 pgs.

"Japanese Application Serial No. 2020-28554, Examiners Decision of Final Refusal dated Sep. 21, 2021", w/ English Translation, 5 pgs.

"U.S. Appl. No. 16/282,760, Final Office Action dated Mar. 24, 2022", 16 pgs.

"U.S. Appl. No. 16/282,760, Response filed Feb. 14, 2022 to Non Final Office Action dated Nov. 12, 2021", 10 pgs.

"European Application Serial No. 20168120.2, Response filed Dec. 2, 2021 to Communication Pursuant to Article 94(3) EPC dated Jul. 26, 2021", 10 pgs.

"Japanese Application Serial No. 2020-071135, Response filed Feb. 16, 2022 to Final Notification of Reasons for Refusal dated Nov. 22, 2021", w/English translation, 4 pgs.

"U.S. Appl. No. 16/282,760, Examiner Interview Summary dated May 19, 2022", 2 pgs.

"U.S. Appl. No. 16/282,760, Non Final Office Action dated Jul. 22, 2022", 11 pgs.

"U.S. Appl. No. 16/282,760, Response filed May 20, 2022 to Final Office Action dated Mar. 24, 2022", 6 pgs.

"European Application Serial No. 20168120.2, Communication Pursuant to Article 94(3) EPC dated May 31, 2022", 5 pgs.

"European Application Serial No. 20168120.2, Response filed Aug. 2, 2022 to Communication Pursuant to Article 94(3) EPC dated May 31, 2022", w/ English claims, 56 pgs.

"Japanese Application Serial No. 2020-71135, Notification of Reasons for Refusal dated Jul. 4, 2022", w/ English translation, 5 pgs.

"U.S. Appl. No. 16/282,760, Advisory Action dated May 27, 2022", 3 pgs.

"U.S. Appl. No. 16/282,760, Examiner Interview Summary dated Oct. 11, 2022", 2 pgs.

"U.S. Appl. No. 16/282,760, Response filed Oct. 19, 2022 to Non Final Office Action dated Jul. 22, 2022", 7 pgs.

"Japanese Application Serial No. 2020-71135, Response filed Oct. 4, 2022 to Notification of Reasons for Refusal dated Jul. 4, 2022", with machine translation, 9 pgs.

"European Application Serial No. 20158849.8, Communication Pursuant to Article 94(3) EPC dated Apr. 5, 2023", 6 pgs.

* cited by examiner

MEDICAL DEVICE

FIELD

The present disclosure relates generally to a medical device. More particularly, the disclosure relates to a microdebrider or shaver configured to be capable of resecting and coagulating tissue in nasal related surgical operations.

BACKGROUND

Surgical apparatus used to shave, cut, resect, abrade and/or remove tissue, bone and/or other bodily materials are known. Such surgical apparatus can include a cutting surface, such as a rotating or reciprocating blade disposed on an elongated inner tube that is rotated within an elongated outer tube having a cutting window. The inner and outer tubes together form a surgical cutting instrument or unit. Microdebrider shaver blades are common instruments used in endoscopic surgery. The shaver blade delivers high speed mechanical cutting of tissue at a specified area of anatomy that the surgeon can reach through a minimally invasive incision or natural orifice. One challenge during procedures using such instruments can be the slowing down or stopping of bleeding (hemostasis) during the procedure. One solution for maintaining proper hemostasis during a procedure is to utilize an electrocautery instrument that can be used inside the same minimally invasive surgical corridor. In a minimally invasive procedure, every time the surgeon exchanges the cutting instrument for the electrocautery instrument there is a corresponding increase in the time required to perform the procedure and there is a risk of traumatizing the anatomy due to the exchange of the instruments. Thus, it is convenient to combine the mechanical cutting and electrocautery instruments to form one instrument performing both functions. By providing a microdebrider shaver blade that also can perform electrocautery, the need to perform tool exchanges at the surgical site is reduced and can even be eliminated.

SUMMARY

In one aspect, the present disclosure provides a medical device. In an embodiment, the medical device comprises a first electrode. In an embodiment, the medical device comprises a first electrode and a second electrode. In an embodiment, the medical device comprises a tubular member. In an embodiment, the medical device comprises an inner tubular member and an outer tubular member. In an embodiment, the medical device comprises a cannulated shaft. In an embodiment, the medical device comprises a cannulated plunger. In an embodiment, the medical device comprises a cannulated armature. In an embodiment, the medical device comprises a handpiece or handle.

In one aspect, the present disclosure provides a medical device comprising a tubular member and a first electrode. In an embodiment, the tubular member is configured to have a proximal end and a distal end with the first electrode disposed at the distal end of the tubular member. In an embodiment, the tubular member is configured to have an open window disposed at the distal end. In an embodiment, the first electrode is configured to encompass the open window of the tubular member. In an embodiment, the open window is configured to be symmetrical or substantially symmetrical along a longitudinal axis of the tubular member. In an embodiment, the first electrode is configured to be symmetrical or substantially symmetrical along a longitudinal axis of the tubular member. In an embodiment, the first electrode is configured to encompass the open window of the tubular member and configured to be symmetrical or substantially symmetrical along a longitudinal axis of the tubular member. In an embodiment, the medical device also comprises a second electrode. In an embodiment, the second electrode is disposed at the distal end of the tubular member. In an embodiment, the second electrode is configured to be symmetrical or substantially symmetrical along a longitudinal axis of the tubular member. In an embodiment, both the first electrode and the second electrode are configured to be symmetrical or substantially symmetrical along a longitudinal axis of the tubular member. In an embodiment, the first electrode is configured to cover the open window area of the tubular member with extension to one side of the distal end of the tubular member and the second electrode configured to be disposed on the opposite side of the distal area of the tubular member when the first or the second electrode is not symmetrical along a longitudinal axis of the outer tubular member.

In one aspect embodiment, the present disclosure provides a medical device comprising an outer tubular member, an inner tubular member, and a first electrode. In an embodiment, the outer tubular member is configured to have a proximal end and a distal end with the first electrode disposed at the distal end of the outer tubular member. In an embodiment, the outer tubular member is configured to have an open window disposed at the distal end of the outer tubular member. In an embodiment, the first electrode is configured to cover the open window of the outer tubular member. In an embodiment, the open window is configured to be symmetrical or substantially symmetrical along a longitudinal axis of the outer tubular member. In an embodiment, the first electrode is configured to be symmetrical or substantially symmetrical along a longitudinal axis of the outer tubular member. In an embodiment, the inner tubular member is configured to have an open distal end. In an embodiment, the inner tubular member is configured to be received within the outer tubular member. In an embodiment, the open window of the outer tubular member and the open distal end of the inner tubular member are configured to form a cutting tool once the medical device is in operation. In an embodiment, the medical device also comprises a second electrode. In an embodiment, the second electrode is disposed at the distal end of the outer tubular member. In an embodiment, the second electrode is configured to be symmetrical or substantially symmetrical along a longitudinal axis of the outer tubular member. In an embodiment, both the first electrode and the second electrode are configured to be symmetrical or substantially symmetrical along a longitudinal axis of the outer tubular member. In an embodiment, the first electrode is configured to cover the open window area of the outer tubular member with extension to one side of the distal end of the outer tubular member and the second electrode configured to cover the opposite side of the distal area of the outer tubular member when the first or the second electrode is not symmetrical along a longitudinal axis of the outer tubular member.

In one aspect, the present disclosure provides a medical device comprising an outer tubular member, an inner tubular member, a cannulated plunger, and a first electrode. In an embodiment, the outer tubular member is configured to have a proximal end and a distal end with the first electrode disposed at the distal end of the outer tubular member. In an embodiment, the outer tubular member is configured to have an open window disposed at the distal end of the outer tubular member. In an embodiment, the first electrode is configured to cover the open window of the outer tubular member. In an embodiment, the open window is configured to be symmetrical or substantially symmetrical along a longitudinal axis of the outer tubular member. In an embodiment, the first electrode is configured to be symmetrical or substantially symmetrical along a longitudinal axis of the outer tubular member. In an embodiment, the inner tubular member is configured to have an open distal end. In an embodiment, the inner tubular member is configured to be received within the outer tubular member. In an embodiment, the open window of the outer tubular member and the open distal end of the inner tubular member are configured to form a cutting tool once the medical device is in operation. In an embodiment, the cannulated plunger is configured to drive the inner tubular member. In an embodiment, the cannulated plunger is configured to reciprocate the inner tubular member. In an embodiment, the cannulated plunger is configured to be used as a suction line. In an embodiment, the cannulated plunger is configured to drive a working member and to function as a suction line as well. In an embodiment, the inner tubular member and the outer tubular member are configured to be a working member. In an embodiment, the medical device also comprises a second electrode. In an embodiment, the second electrode is disposed at the distal end of the outer tubular member. In an embodiment, the second electrode is configured to be symmetrical or substantially symmetrical along a longitudinal axis of the outer tubular member. In an embodiment, both the first electrode and the second electrode are configured to be symmetrical or substantially symmetrical along a longitudinal axis of the outer tubular member. In an embodiment, the first electrode is configured to cover the open window area of the outer tubular member with extension to one side of the distal end of the outer tubular member and the second electrode configured to cover the opposite side of the distal area of the outer tubular member when the first or the second electrode is not symmetrical along a longitudinal axis of the outer tubular member.

In one aspect, the present disclosure provides a medical device comprising an outer tubular member, an inner tubular member, a cannulated armature and a first electrode. In an embodiment, the outer tubular member is configured to have a proximal end and a distal end with the first electrode disposed at the distal end of the outer tubular member. In an embodiment, the outer tubular member is configured to have an open window disposed at the distal end of the outer tubular member. In an embodiment, the first electrode is configured to cover around the open window of the outer tubular member. In an embodiment, the open window is configured to be symmetrical or substantially symmetrical along a longitudinal axis of the outer tubular member. In an embodiment, the first electrode is configured to be symmetrical or substantially symmetrical along a longitudinal axis of the outer tubular member. In an embodiment, the inner tubular member is configured to have a distal end and an open window disposed at the distal end. In an embodiment, the inner tubular member is configured to be received within the outer tubular member. In an embodiment, the open window of the outer tubular member and the open window of the inner tubular member are configured to form a cutting tool when the medical device is in operation. In an embodiment, the cannulated armature is configured to drive the inner tubular member. In an embodiment, the cannulated armature is configured to oscillate or rotate the inner tubular member. In an embodiment, the cannulated armature is configured to be used as a suction line. In an embodiment, the cannulated armature is configured to drive a working member and to function as a suction line as well. In an embodiment, the inner tubular member and the outer tubular member are configured to be a working member. In an embodiment, the medical device also comprises a second electrode. In an embodiment, the second electrode is disposed at the distal end of the outer tubular member. In an embodiment, the second electrode is configured to be symmetrical or substantially symmetrical along a longitudinal axis of the outer tubular member. In an embodiment, both the first electrode and the second electrode are configured to be symmetrical or substantially symmetrical along a longitudinal axis of the outer tubular member. In an embodiment, the first electrode is configured to cover the open window area of the outer tubular member with extension to one side of the distal end of the outer tubular member and the second electrode configured to cover the opposite side of the distal area of the outer tubular member when the first or the second electrode is not symmetrical along a longitudinal axis of the outer tubular member.

In one aspect, the present disclosure provides a medical device comprising an inner tubular member, an outer tubular member, a motor assembly, a first electrode, and a handpiece. In an embodiment, the outer tubular member is configured to have a proximal end and a distal end with a first electrode disposed at the distal end of the outer tubular member. In an embodiment, the outer tubular member is configured to have an open window disposed at the distal end of the outer tubular member. In an embodiment, the first electrode is configured to cover the open window of the outer tubular member. In an embodiment, the open window is configured to be symmetrical or substantially symmetrical along a longitudinal axis of the outer tubular member. In an embodiment, the first electrode is configured to be symmetrical or substantially symmetrical along a longitudinal axis of the outer tubular member. In an embodiment, the inner tubular member is configured to have a distal end and an open window disposed at the distal end. In an embodiment, the inner tubular member is configured to be received within the outer tubular member. In an embodiment, the open window of the outer tubular member and the open window of the inner tubular member are configured to form a cutting tool when the medical device is in operation. In an embodiment, the motor assembly is configured to drive the inner tubular member. In an embodiment, the inner tubular member is configured to be connectable to a suction line. In an embodiment, both the inner tubular member and the outer tubular member are configured to be detachable from the handpiece. In an embodiment, both the inner tubular member and the outer tubular member are configured to be fixedly attached to the handpiece. In an embodiment, the medical device also comprises a second electrode. In an embodiment, the second electrode is disposed at the distal end of the outer tubular member. In an embodiment, the second electrode is configured to be symmetrical or substantially symmetrical along a longitudinal axis of the outer tubular member. In an embodiment, both the first electrode and the second electrode are configured to be symmetrical or substantially symmetrical along a longitudinal axis of the outer tubular member. In an embodiment, the first electrode is configured to cover the open window area of the outer tubular member with extension to one side of the distal end of the outer tubular member and the second electrode configured to cover the opposite side of the distal area of the outer tubular member when the first or the second electrode is not symmetrical along a longitudinal axis of the outer tubular member.

In one aspect, the present disclosure provides a medical device comprising: an inner tubular member, an outer tubular member, a cannulated armature, a first electrode, a second electrode and a handpiece. In an embodiment, the inner tubular member is configured to have an open window at its distal end. In an embodiment, the inner tubular member is configured to be operably connected to the cannulated armature. In an embodiment, the outer tubular member is configured to have a distal end and an open window disposed at the distal end. In an embodiment, the open window of the inner tubular member and the open window of the outer tubular member are configured to form a cutting tool when the medical device is in operation. In an embodiment, the first electrode is configured to be disposed at the distal end of the outer tubular member. In an embodiment, the inner tubular member is configured to be received within the outer tubular member. In an embodiment, the first electrode is configured to wrap around the open window of the outer tubular member. In an embodiment, the open window of the outer tubular member is configured to be symmetrical or substantially symmetrical along the longitudinal axis of the outer tubular member. In an embodiment, the first electrode is configured to be symmetrical or substantially symmetrical along the longitudinal axis of the outer tubular member. In an embodiment, the cannulated armature is configured to be used as a suction line. In an embodiment, the cannulated armature is configured to drive a working member and to function as a suction line as well. In an embodiment, the inner tubular member and the outer tubular member are configured to be a working member. In an embodiment, both the inner tubular member and the outer tubular member are configured to be detachable from the housing. In an embodiment, both the inner tubular member and the outer tubular member are configured to be fixedly attached to the handpiece. In an embodiment, the medical device also comprises a second electrode. In an embodiment, the second electrode is disposed at the distal end of the outer tubular member. In an embodiment, the second electrode is configured to be symmetrical or substantially symmetrical along a longitudinal axis of the outer tubular member. In an embodiment, both the first electrode and the second electrode are configured to be symmetrical substantially symmetrical along a longitudinal axis of the outer tubular member. In an embodiment, the first electrode is configured to cover the open window area of the outer tubular member with extension to one side of the distal end of the outer tubular member and the second electrode configured to cover the opposite side of the distal area of the outer tubular member when the first or the second electrode is not symmetrical along a longitudinal axis of the outer tubular member.

In another aspect, the present disclosure provides a method of making a medical device as described herein. In an embodiment, the method includes making a medical device with a first electrode disposed at the distal end of the tubular member as described herein. In an embodiment, the present disclosure also provides a method of making a medical device with a first electrode and a second electrode disposed at the distal end of the tubular member as described herein. In an embodiment, the method includes making a medical device as described herein by using a microfabrication process. In an embodiment, the method includes making a medical device as described herein by employing a flexible circuit process. In an embodiment, the method includes making a medical device as described herein by employing a conductive ink process.

DETAILED DESCRIPTION

Figure 1:
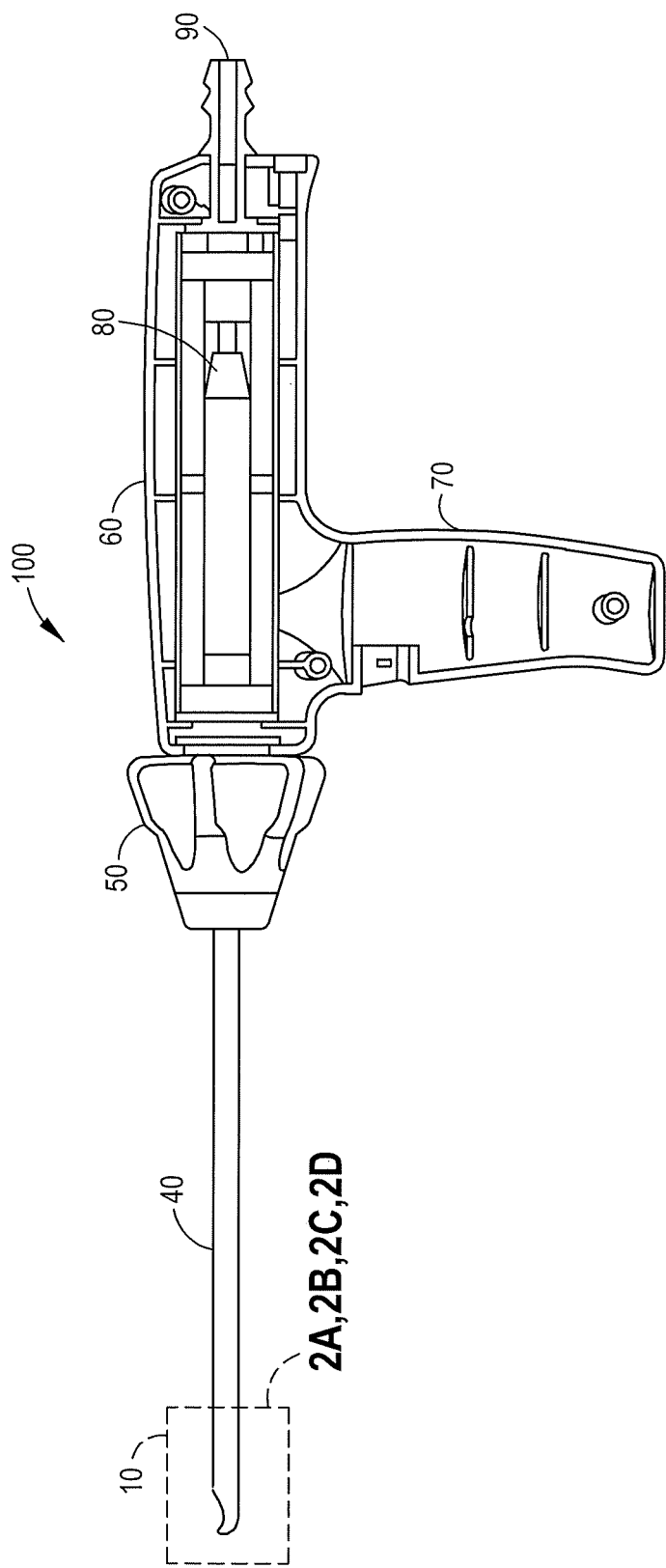
FIG. 1 is a partial sectional view of a medical device in accordance with one aspect of the present disclosure.

FIG. 1 is a partial sectional view of a medical device in accordance with one exemplary embodiment of the present disclosure. The medical device 100 of FIG. 1 generally includes a working tip section 10, a tubular section 40, a nosecone 50, a housing 60, a handle grip 70 (optional), a cannulated plunger 80, and a suction connector 90.

In the above exemplary embodiment, the tubular section 40 may be configured to comprise an outer tubular member 20 (not shown in FIG. 1) and an inner tubular member 30 (not shown in FIG. 1). The outer tubular member 20 may be mounted to the housing 60 through the nosecone 50 and acts as a static member, wherein the inner tubular member 30 is received inside the outer tubular member 20, and is configured to be axially movable within the outer tubular member 20. It should be understood that the outer tubular member 20 may be rotatably, detachably or fixedly mounted to the housing 60. The inner tubular member 30 may be configured to be connected to the cannulated plunger 80. The cannulated plunger 80 is configured to be connectable to a suction source through the connector 90. In the above embodiments, the inner diameter of the outer tubular member 20 may be configured to be slightly larger than the outer diameter of the inner tubular member 30 (for example, by approximately 0.002 inches). This allows the inner tubular member 30 to move freely to help minimizing wobbling of the inner tubular member 30 to keep the open distal end of the inner tubular member closely aligned with the open window of the outer tubular member.

In the above exemplary embodiment, the tubular section 40 may be configured as one piece, and detachable/attachable from/to the housing 60. The tubular section 40 may be made disposable or reusable. The nosecone 50 may be configured to rotate the tubular section 40 in addition to being as a coupler between the tubular section 40 and the housing 60. In particular, the nosecone 50 may be configured to be capable of rotating the outer tubular member to a certain desirable position to align the outer tubular member with the inner tubular member. The nosecone 50 may be made disposable or reusable. The cannulated plunger 80 may be powered by means known in the art such as solenoids connected to a power source. The housing 60 may be made disposable or reusable. The hand grip 70 may be configured to be optional, rendering the handpiece to be a linear type. The medical device 100 itself may be made disposable or reusable, and preferably disposable.

Further information about this type of medical device using reciprocating mode for cutting may also be found in a U.S. application Ser. No. 15/880,998 filed on Jan. 26, 2018, the contents of which are incorporated herein in its entirety by reference.

Figure 2A:
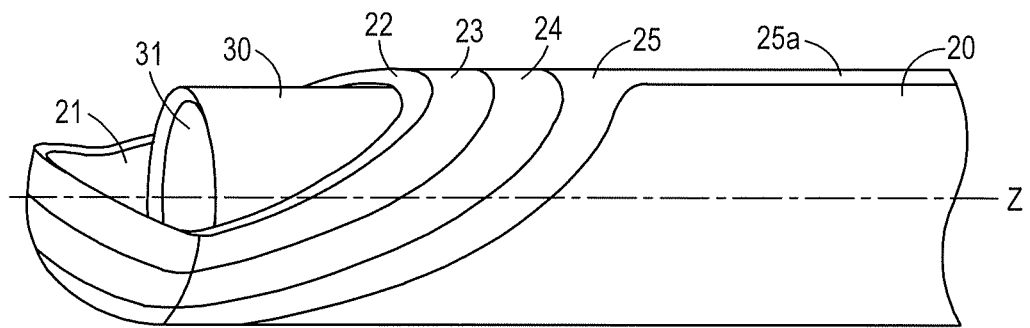
FIG. 2A, FIG. 2B, FIG. 2C, and FIG. 2D are partial schematic views of the various features of the working tip section of the medical device of FIG. 1.
Figure 2B:
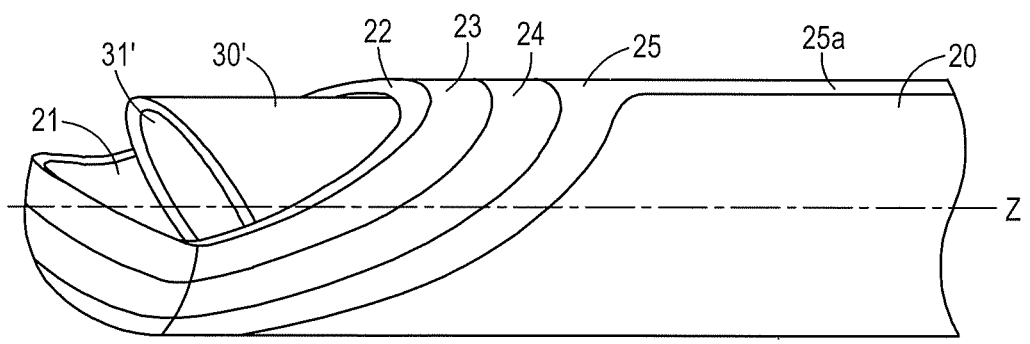

FIG. 2A, FIG. 2B, FIG. 2C, and FIG. 2D illustrate some exemplary embodiments of a working tip section 10 of a medical device 100 in accordance with some aspects of the present disclosure. More particularly, FIG. 2A and FIG. 2B show exemplary embodiments of a working tip section with an outer tubular member 20 having a symmetrical or substantially symmetrical open window and symmetrical or substantially symmetrical electrodes disposed at the distal end while the inner tubular member has different distal configurations. For both FIG. 2A and FIG. 2B, the outer tubular member 20 has an open window 21 disposed at the distal end of the outer tubular member 20. The open window 21 has a surface area 22. The surface area 22 may be preferably configured to have a sharp edge, in particular towards the distal most end. The open window 21 is configured to be symmetrical or substantially symmetrical along a longitudinal axis Z. Even though the open window 21 is shown to be disposed at the distal most end, it may also be disposed at a location with some distance away from the farthest end. A first electrode is disposed at the distal end of the outer tubular member 20. It is configured to cover the surface area 22 and its neighboring region 23 of the outer tubular member 20. It may also be stated as that the first electrode is configured to encircle, enclose, surround, envelop, hem in, or wrap around the open window 21 or its neighboring region 23. It is also contemplated that the first electrode may only cover the surface area 22 of the open window 21 without extending to its surrounding area 23. The first electrode is configured to be symmetrical or substantially symmetrical along the longitudinal axis Z. The tip section of FIG. 2A or FIG. 2B is also configured to have an insulating zone 24. The insulation zone 24 may also be configured to be symmetrical or substantially symmetrical along the longitudinal axis Z. The insulation zone 24 may be configured to surround the first electrode with a constant gap to the first electrode all around. A second electrode 25 is disposed on a dielectric layer and configured to surround the insulation zone 24. The second electrode 25 is configured to have a runner 25a which is preferably configured to be parallel to the longitudinal axis Z. The second electrode 25 is configured to be symmetrical or substantially symmetrical along the longitudinal axis Z. The runner 25a may be preferably configured to equally or substantially equally bisect the open window 21 even though other configurations may also be contemplated. The runner 25a is configured to be connectable to a metallic wire. The second electrode 25 is preferably configured to surround the insulation zone 24 and maintain a constant gap with the insulation zone 24 all around to achieve a more desirable function. The first electrode and the second electrode are configured to form a bipolar RF device for cutting and/or coagulating purpose. The outer tubular member 20 may be made of metallic or polymeric materials. When a metallic material such as stainless steel is used, the first electrode may be formed around the open window and its neighboring area of the outer tubular member by putting an insulation layer around the outer tubular member. The second electrode may then be formed by putting conductive materials such as silver, gold, and solder on the insulation layer even though gold may be preferred as conductive material. The outer tubular member may be made rigid, malleable, or flexible depending on the needs and functions of the medical device. Yet, the outer tubular member may be preferred to be rigid.

FIG. 2A and FIG. 2B also demonstrate different embodiments of the inner tubular member of the working tip 10 of a medical device 100. FIG. 2A illustrates an inner tubular member 30 with a circular open end 31. The circular open end 31 is configured to have a sharp edge. This sharp edge is intended to form a cutting tool with the open window 21 of the outer tubular member 20 once the inner tubular member 30 is reciprocated by a mechanism such as a plunger and solenoid combination during a surgical operation. It may be more preferable to have a sharper surface area at the distal most end of the open window 21 of the outer tubular member in order to have a better cutting effect with the open end 31. FIG. 2B illustrates an inner tubular member 30' with a beveled open end 31'. The beveled open end 31' is configured to have a sharp edge. This sharp edge is intended to form a cutting tool with the open window 21 of the outer tubular member 20 once the inner tubular member 30' is reciprocated by a mechanism such as a plunger and solenoid combination during a surgical operation. It is contemplated that the outer tubular member 20 or the inner tubular member 30' may be rotated/adjusted, for example, through a nosecone 50, to align the open window 21 with the beveled distal end 31' to achieve more desirable cutting effect since it may become necessary due to the beveled nature of the inner tubular member 30'. The inner tubular member 30 or 30' may be made of stainless steel or other metallic or strong materials so long as it can perform efficient cutting. The inner tubular member may be made rigid, malleable, or flexible depending on the needs and functions of the medical device. Yet, the inner tubular member may be preferred to be rigid.

Figure 2C:
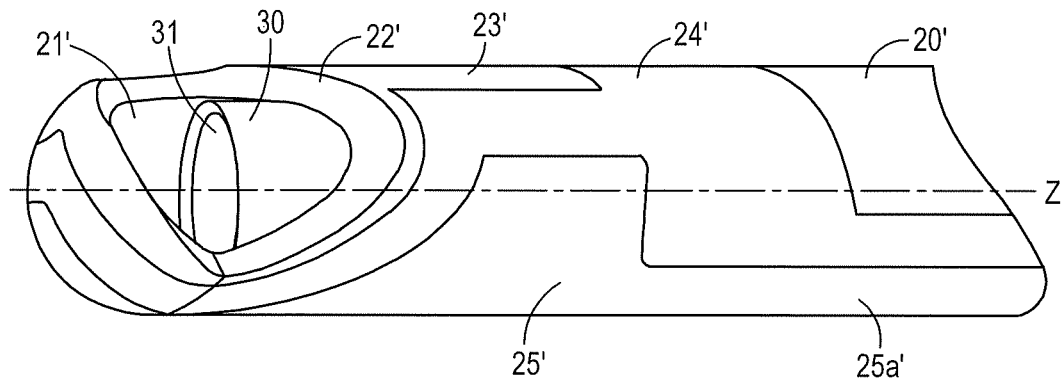
Figure 2D:
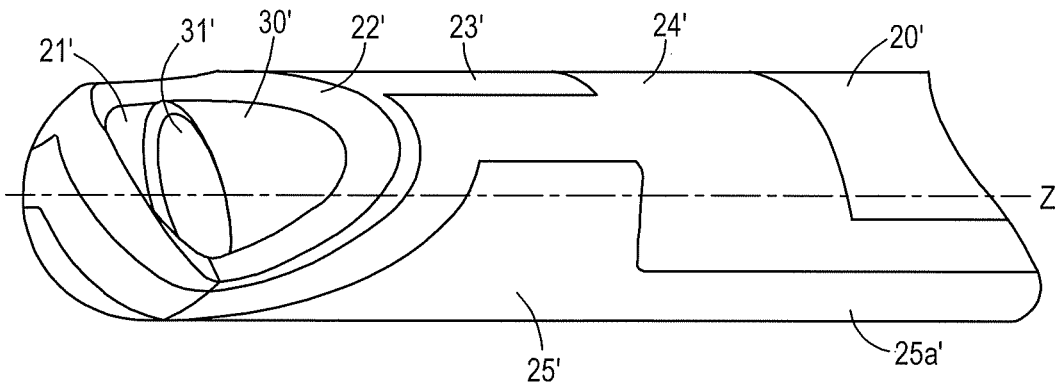

FIG. 2C and FIG. 2D demonstrate further embodiments of a working tip section with an outer tubular member 20' having a symmetrical open window with an asymmetrical electrode assembly while the inner tubular member has different distal configurations. More particularly, FIG. 2C and FIG. 2D both have an outer tubular member 20' with an open window 21' disposed at the distal end of the open window 21'. The open window 21' is configured to have a surface area 22'. The surface area 22' may be preferably configured to have a sharp edge, in particular towards the distal most end. The open window 21' may be preferably configured to be symmetrical or substantially symmetrical along a longitudinal axis Z even though other geometry or configurations are also contemplated. Even though the open window 21' is shown to be disposed at the distal most end, it may be disposed at a location with some distance away from the farthest end. A first electrode is configured to cover the surface area 22' and the shaded area 23' at the distal end of the outer tubular member 20'. The shaded area 23' is disposed on one side of the outer tubular member 20'. Consequently, the first electrode is configured to cover the surface area 22' and extend from the surface area 22' to one side of the outer tubular member 20'. A second electrode 25' is disposed on a dielectric layer on the other side of the outer tubular member 20'. An insulation zone 24' is disposed between the first electrode 23' and the second electrode 25'. The second electrode 25' is configured to have a runner 25'a configured to be connectable to a metallic wire. The first electrode 23' and the second electrode 25' are configured to form a bipolar RF device for cutting and/or coagulating purpose. The outer tubular member 20' may be made of metallic or polymeric materials. When a metallic material such as stainless steel is used, the first electrode may be formed around the open window and its neighboring area of the outer tubular member by putting an insulation layer around the distal end of the outer tubular member in a manner as insulation zone 24'. The second electrode may then be formed on the other side of the distal end of the outer tubular member. It may also be formed by putting conductive materials such as silver, gold, and solder on the extended insulation layer even though gold may be preferred as conductive material. The outer tubular member may be made rigid, malleable, or flexible depending on the needs and functions of the medical device. Yet, the outer tubular member may be preferred to be rigid.

FIG. 2C and FIG. 2D also show different embodiments of the inner tubular member of the working tip 10 of a medical device 100. FIG. 2C illustrates an inner tubular member 30 with a circular open end 31. The circular open end 31 is configured to have a sharp edge. This sharp edge is intended to form a cutting tool with the open window 21' of the outer tubular member 20' once the inner tubular member 30 is reciprocated by a mechanism such as a plunger and solenoid combination during a surgical operation. It may be more preferable to have a sharper surface area at the distal most end of the open window 21' of the outer tubular member in order to have a better cutting effect with the open end 31. FIG. 2D illustrates an inner tubular member 30' with a beveled open end 31'. The beveled open end 31' is configured to have a sharp edge. This sharp edge is intended to form a cutting tool with the open window 21' of the outer tubular member 20' once the inner tubular member 30' is reciprocated by a mechanism such as a plunger and solenoid combination during a surgical operation. It is contemplated that the outer tubular member 20' and/or the inner tubular member 31' may be rotated/adjusted, for example, through a nosecone 50, to align the open window 21' with the beveled distal end 31' to achieve more desirable cutting effect since it may become necessary due to the beveled nature of the inner tubular member 30'. The inner tubular member 30 or 30' may be made of stainless steel or other metallic or strong materials so long as it can perform efficient cutting. The inner tubular member may be made rigid, malleable, or flexible depending on the needs and functions of the medical device. Yet, the inner tubular member may be preferred to be rigid.

Figure 3:
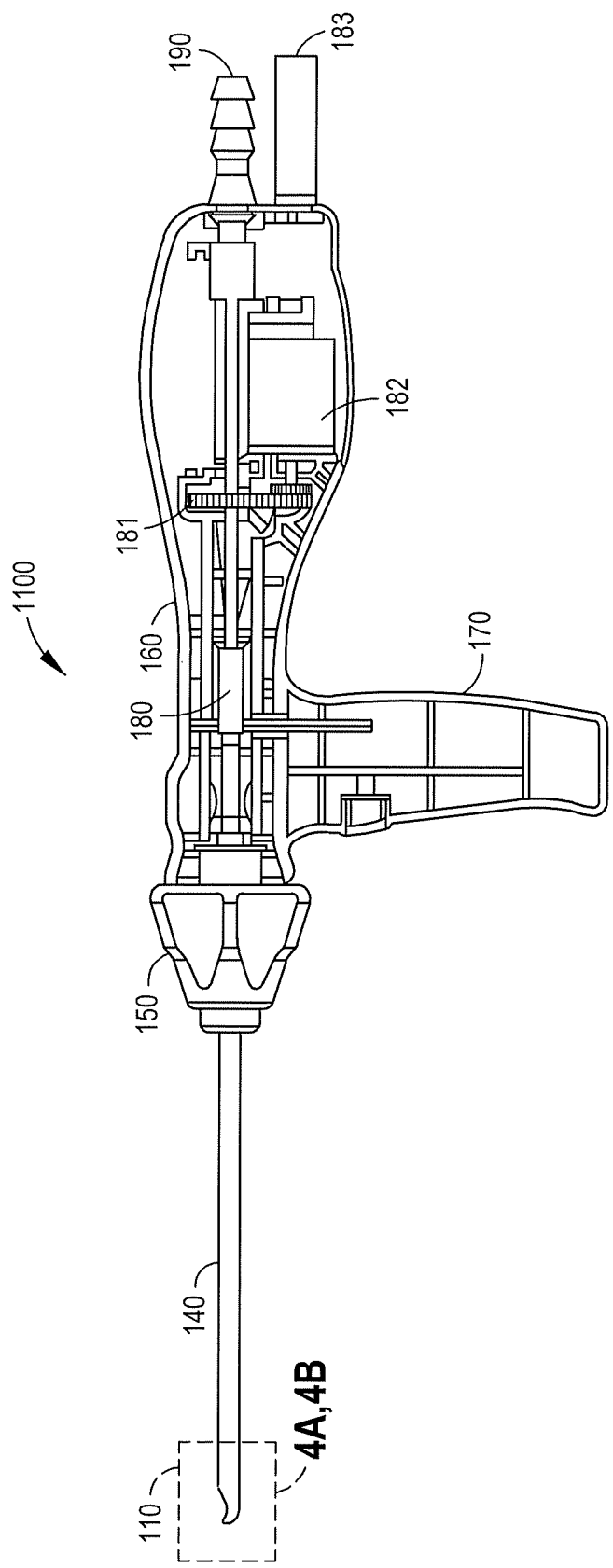
FIG. 3 is a partial sectional view of a medical device in accordance with another aspect of the present disclosure.

FIG. 3 is a partial sectional view of a medical device in accordance with another exemplary embodiment of the present disclosure. The medical device 1100 of FIG. 3 generally includes a working tip portion 110, a tubular section 140, a nosecone 150, a housing 160, a handle grip 170 (optional), a cannulated shaft 180, a gear set 181, a motor set 182, and a power connector 183, and a suction connector 190.

In the above exemplary embodiment, the tubular section 140 may be configured to comprise an outer tubular member 120 (not shown in FIG. 3) and an inner tubular member 130 (not shown in FIG. 3). The outer tubular member 120 may be mounted to the housing 160 through the nosecone 150 and acts as a static member, wherein the inner tubular member 130 is received inside the outer tubular member 120, and is configured to be rotatable and/or translational within the outer tubular member 120. It should be understood that the outer tubular member 120 may be rotatably, detachably or fixedly mounted to the housing 160. The inner tubular member 130 may be configured to be connected to the cannulated shaft 180. The cannulated shaft 180 is rotated or oscillated and/or translated by the motor set 182 through a gear set 181. The motor set 182 is configured to be powered by a power source through the power connector 183.

In the above exemplary embodiment, the tubular section 140 may be configured as one piece, and detachable/attachable from/to the housing 160. The tubular section 140 may be made disposable or reusable. The nosecone 150 may be configured to rotate the tubular section 140 in addition to being as a coupler between the tubular section 140 and the housing 160. In particular, the nosecone 150 may be configured to be capable of rotating the outer tubular member to a certain desirable position to align the outer tubular member with the inner tubular member. The hand grip 170 may be configured to be optional, rendering the handpiece to be a linear type. The housing 160 may be made disposable or reusable. The medical device 1100 itself may be made disposable or reusable, and preferably disposable.

Figure 4A:
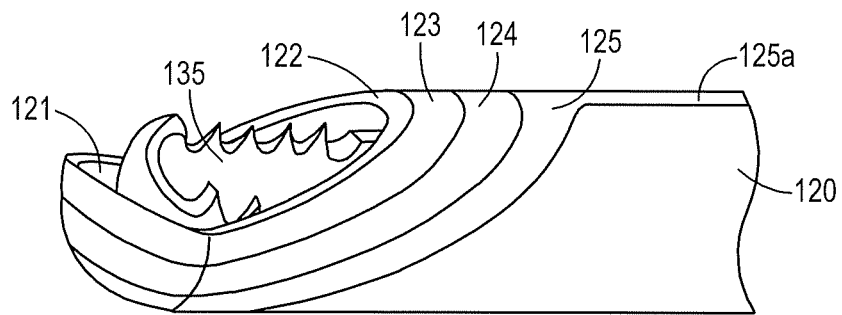
FIG. 4A and FIG. 4B. are partial schematic views of the various features of the working tip section of the medical device of FIG. 3.
Figure 4B:
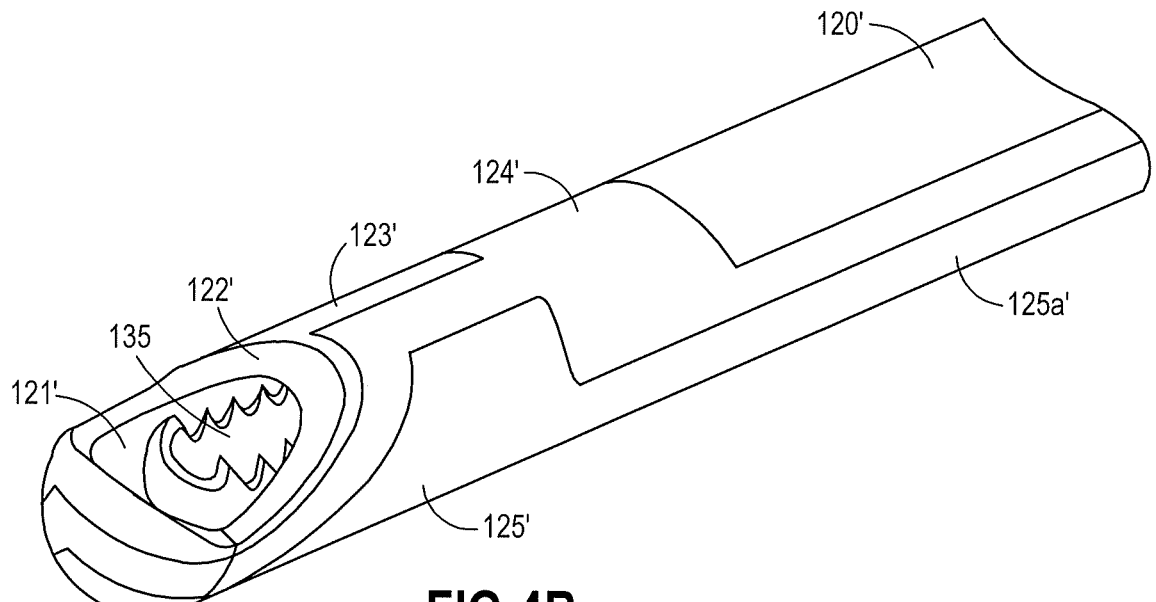

FIG. 4A, and FIG. 4B illustrates some embodiments of a working tip section 110 of a medical device 1100 of FIG. 3. More particularly, FIG. 4A illustrates a working tip having an outer tubular member 120 as identically or similarly described with respect to the outer tubular member 20 of FIG. 2A or FIG. 2B. Consequently, all the features that the outer tubular member 20 has should be equally applicable to the outer tubular member 120. Even though FIG. 4A only shows an inner tubular member 130 (not numbered in FIG. 4A or FIG. 4B) having a distal open window 135 with toothed edges, it should be understood that other types of window shapes and/or configurations are also contemplated. The inner tubular member 130 is configured to be rotatable and/or capable of translation within the outer tubular member 120. FIG. 4B illustrates a working tip having an outer tubular member 120' as identically or similarly described with respect to the outer tubular member 20' of FIG. 2C or FIG. 2D. Consequently, all the features that the outer tubular member 20' has should be equally applicable to the outer tubular member 120'. Even though FIG. 4B only shows an inner tubular member 130 having a distal open window 135 with toothed edges, it should be understood that other types of window shapes and/or configurations are also contemplated. The inner tubular member 130 is configured to be rotatable and/or capable of translation within the outer tubular member 120'. The inner tubular member 130 may be made of stainless steel or other metallic or strong materials so long as it can perform efficient cutting. The inner tubular member may be made rigid, malleable, or flexible depending on the needs and functions of the medical device. Yet, the inner tubular member may be preferred to be rigid.

Figure 5A:
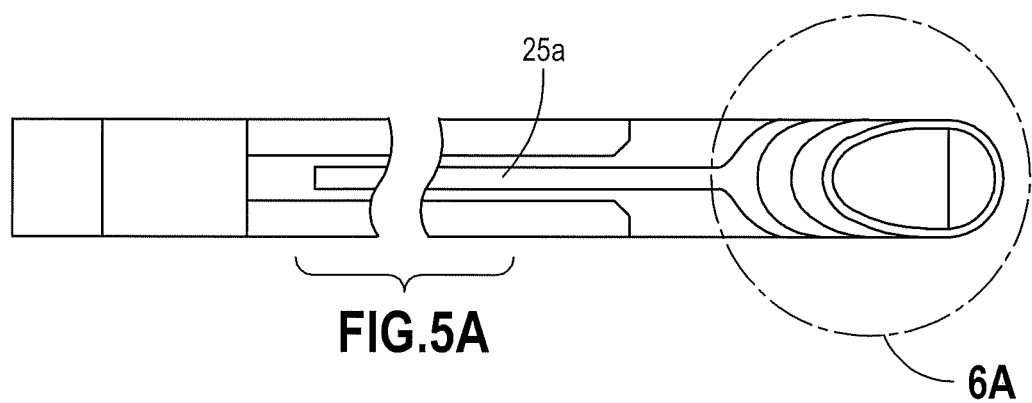
FIG. 5A, FIG. 5B, and FIG. 5C are, respectively, top, side and bottom schematic views of the outer tubular member incorporating some of the symmetrical electrode features of the present disclosure.
Figure 5B:
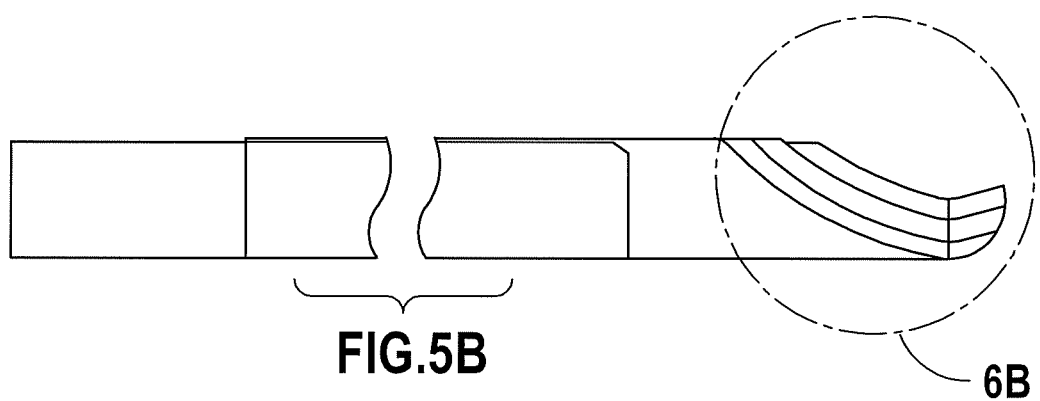
Figure 5C:
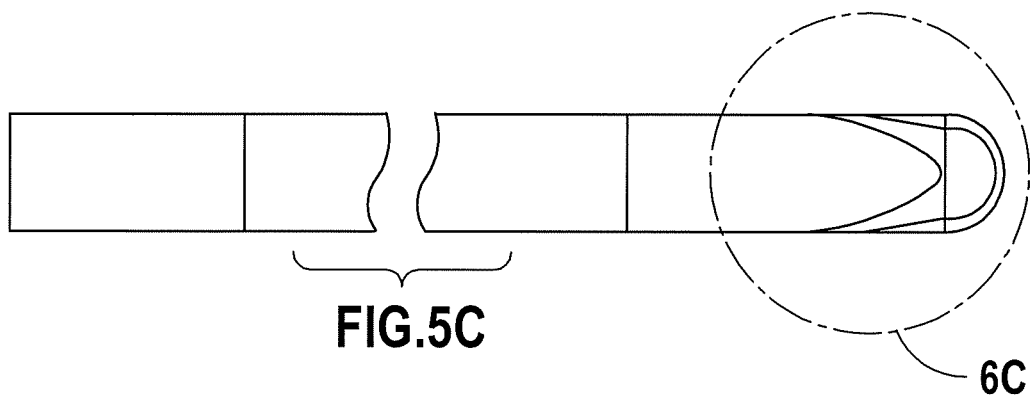
Figure 6A:
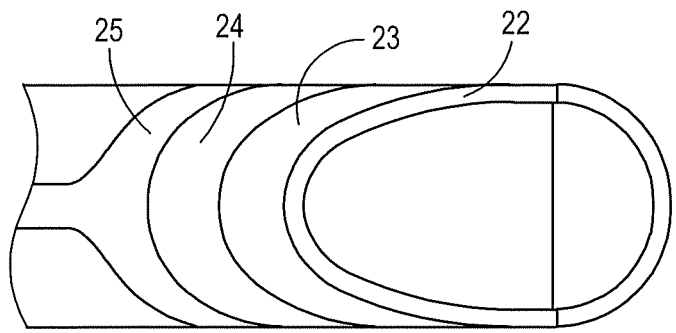
FIG. 6A, FIG. 6B, and FIG. 6C are corresponding expanded views of the tip portions of FIG. 5A, FIG. 5B, and FIG. 5C, respectively.
Figure 6B:
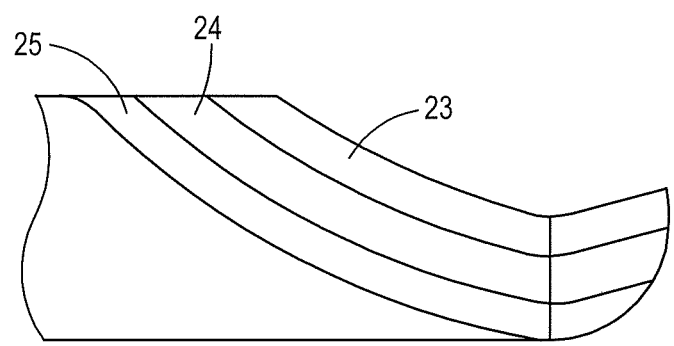
Figure 6C:
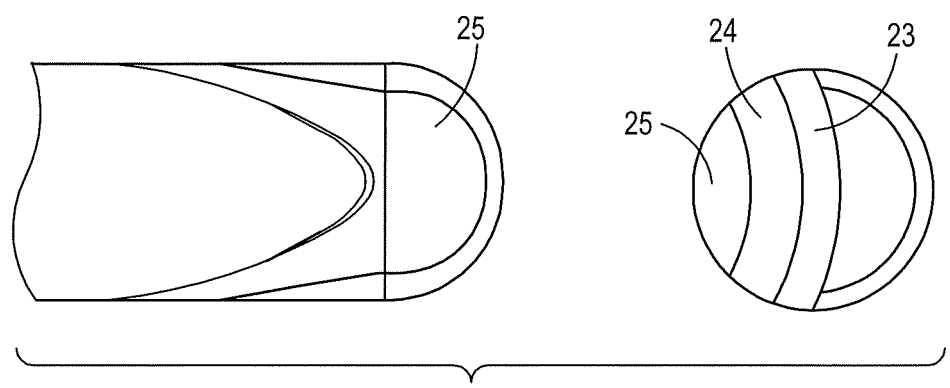

FIG. 5A, FIG. 5B, FIG. 5C, FIG. 6A, FIG. 6B, and FIG. 6C are further detailed illustrations of an outer tubular member 20 or 120 as identically or similarly described with respect to FIG. 2A, FIG. 2B, and FIG. 4A. More particularly, FIG. 5A is a top view of an outer tubular member 20 or 120. FIG. 5B is a side view of an outer tubular member 20 or 120. FIG. 5C is a bottom view of an outer tubular member 20 or 120. FIG. 6A is an expanded top view of the tip portion A of the outer tubular member 20 or 120 of FIG. 5A. FIG. 6B is an expanded side view of the tip portion B of the outer tubular member 20 or 120 of FIG. 5B. The left drawing of FIG. 6C is an expanded bottom view of the tip portion C of the outer tubular member 20 or 120 of FIG. 5C, and the right drawing of FIG. 6C is an expanded end view of the tip portion C of the outer tubular member 20 or 120 of FIG. 5C. FIG. 6A, FIG. 6B, and FIG. 6C show some preferable relative ratios of first electrode 23 or 123, insulating zone 24 or 124, and the second electrode 25 or 125 even though other ratios are also contemplated, for example, a ratio of 0.026 to 0.030 to 0.026 may be preferred between the first electrode 23 or 123, the insulating layer 24 or 124, and the second electrode 25 or 125. Furthermore, for the second electrode 25 or 125, an expanded conductive area as illustrated in the left figure of FIG. 6C for increased contact may be preferable since this allows broader cutting or coagulation. An outer tubular member 20 or 120 such as disclosed in the above figures may be preferably suitable to have an outer diameter of about 4 mm for a microdebrider or shaver.

Figure 7A:
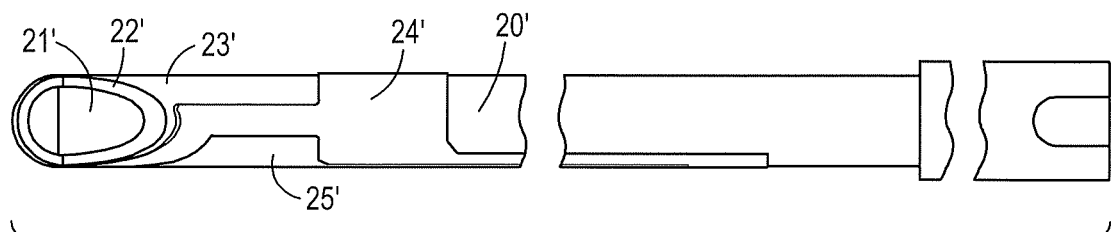
FIG. 7A, FIG. 7B, and FIG. 7C are, respectively, top, side and bottom schematic views of the outer tubular member incorporating some of the electrode design features of the present disclosure.
Figure 7B:
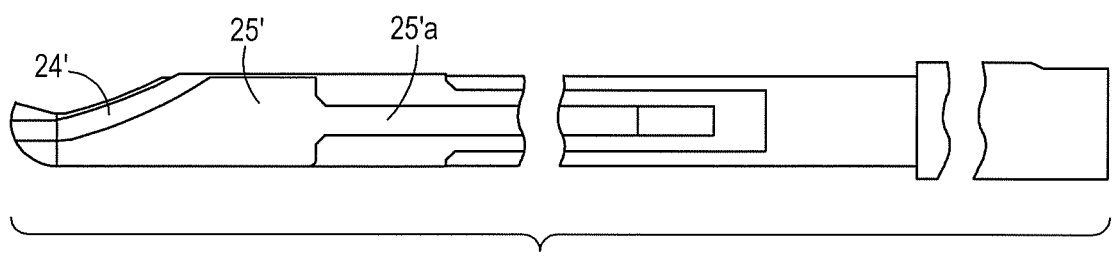
Figure 7C:
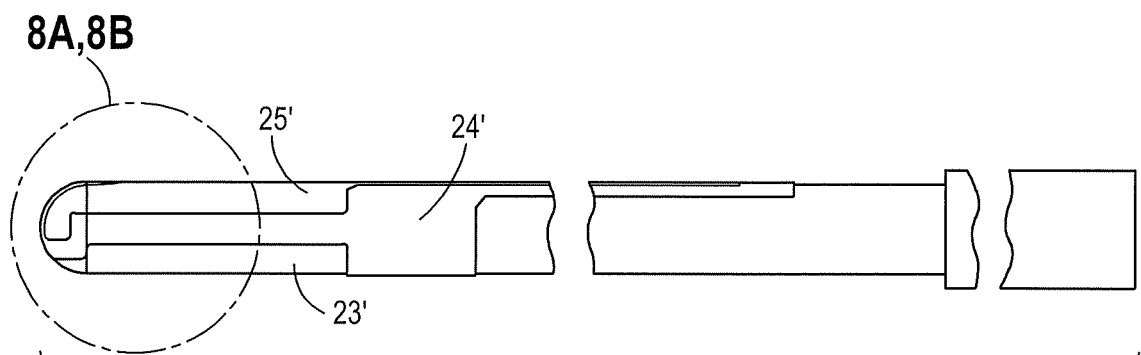
Figure 8A:
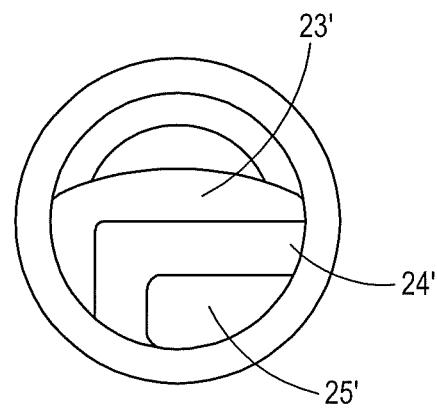
FIG. 8A, and FIG. 8B are the corresponding expanded views of the tip portion of FIG. 7C.
Figure 8B:
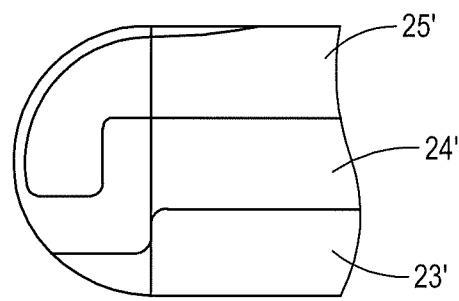

FIG. 7A, FIG. 7B, FIG. 7C, FIG. 8A, and FIG. 8B are further detailed illustrations of an outer tubular member 20' or 120' as identically or similarly described with respect to FIG. 2C, FIG. 2D, and FIG. 4B. More particularly, FIG. 7A is a top view of an outer tubular member 20' or 120'. FIG. 7B is a side view of an outer tubular member 20' or 120'. FIG. 7C is a bottom view of an outer tubular member 20' or 120'. FIG. 8A is an expanded end view of the tip portion of the outer tubular member 20' or 120'. FIG. 8B is an expanded bottom view of the tip portion of the outer tubular member 20' or 120' of FIG. 7C. FIG. 7A, FIG. 7B, FIG. 7C, FIG. 8A, and FIG. 8B show some preferable relative ratios of first electrode 23' or 123', insulating zone 24' or 124', and the second electrode 25' or 125' even though other ratios are also contemplated. An outer tubular member 20' or 120' such as disclosed in the above figures may be preferably suitable to have an outer diameter of about 2 mm for a microdebrider or shaver. Even though FIG. 7B shows an example of runner 25'a disposed on the side of the outer tubular member for this asymmetrical bipolar electrode configuration, it should be understood that the runner 25'a may be disposed along the longitudinal axis in a manner that it equally or substantially equally bisects the open window 21' of the outer tubular member. It is contemplated that doing so will allow an operator to better determine the orientation of the open window, and it may also help the operator to determine how far the operator may insert the tubular member into a surgical area such as for a turbinate surgical operation based on an insertion situation of the runner 25'a. Put it another way, the runner 25'a may be additionally used as a marking tool for an operator to align the open window and/or insertion estimation during an operation. In an embodiment, the runner 25'a may be preferably disposed equally or substantially equally bisecting the open window for an outer tubular member with about 2 mm outer diameter.

In the above embodiments, the outer tubular member has a distal portion and a proximal portion. The proximal portion is configured to be fixedly or detachably connectable to the handpiece, and the distal portion is configured to have an open window. The open window of the outer tubular member is configured to admit or receive tissue to be cut for a surgical operation such as a nasal operation. The cut tissue fragments are then drawn through the lumen of the inner tubular member by suction applied at a suction connector. In the above embodiments, the outer tubular member may be configured to be stationary. The inner tubular member may be preferably configured to be open or to have an open window at its distal end. The inner tubular member may be configured to have a circular sharpened edge or a beveled sharpened edge or other suitable sharp edges such as serrated or knife type of edges if it has an open distal end. It may be configured to have a type of toothed or serrated sharp edges if it is configured to have an open window disposed along its distal end. It should be understood that the outer tubular member may be configured to have more than one window at its distal end. It should also be understood that a bit larger open window may help admitting more tissue for cutting while a smaller window may facilitate a better suction. Accordingly, the open window of the outer tubular member may be sized/shaped/configured/dimensioned in accordance with the needs and/or functions of the medical device even though the open window is preferably configured to be symmetrical or substantially symmetrical along the longitudinal axis of the outer tubular member.

In the above embodiments, the inner tubular member has a distal portion and a proximal portion. The proximal portion may be configured to be operably connectable to a cannulated plunger or cannulated armature or cannulated shaft. The distal portion may be preferably configured to have an open distal end if it is used in a reciprocating mode. The open distal end may be configured to be any suitable sharp edge for cutting purpose. For example, it may be configured to be circular with sharp edge. It may be configured to have beveled sharp edge. The bevel angle may be, for example, at 45° degree in relation to the longitudinal axis. The inner tubular member may be configured to be movable relative to the outer tubular member. The distal portion may be preferably configured to have an open window at the distal end if it is used to be rotated or oscillated and/or translated. The open window may be preferably configured to be symmetrical or substantially symmetrical along the longitudinal axis. The open window may be configured to have toothed type of edge or other suitable sharp edge. The inner tubular member is preferably configured to be flexible. In the above embodiments, the open distal end of the inner tubular member and the open window of the outer tubular member are configured to form a cutting tool or device during an operation of the device.

In the above embodiments wherein the open window of the outer tubular member is intended to be used as part of a cutting tool of the medical device, the open window of the outer tubular member may be configured to have an outer surface edge and an inner surface edge. The outer surface edge may be preferably configured to be smooth in order for it not to cause damage or harm to the tissue/passage way when the device is in the process of being inserted. The inner surface edge, in particular towards the distal end, may be preferably configured to be sharp so that the sharp edge may form a more efficient cutting tool with the sharp edge of the open distal end of the inner tubular member. Similarly, the open distal end of the inner tubular member may be configured to have an outer surface edge and an inner surface edge. The outer surface edge may be preferably configured to be sharp in order for it to form a more efficient cutting tool with the inner surface edge of the outer tubular member.

In the above embodiments wherein the open window of the outer tubular member is intended to be used primarily as admitting tissue to be cut, the open window of the outer tubular member may be configured to have smooth edges while the inner tubular member is then configured to have an open window. In such embodiments, the inner tubular member is configured to be rotatory/oscillatory and/or translational within the outer tubular member. The open window of the inner tubular member is configured to have toothed edges or other sharp edges capable of cutting tissue while being rotated or oscillated. It should be understood that other shapes or configurations are also contemplated for the open window of the inner tubular member.

In the above embodiments, the tubular section may also be configured to comprise more than two tubular members such as an inner tubular member, an outer tubular member and an intermediary tubular member. In such embodiments, either the inner tubular member or the intermediary tubular member may be configured to be operably connectable to the cannulated shaft of the medical device. The inner tubular member or the intermediary tubular member may also be configured to be operably connectable to a motor. In such embodiments, the intermediary tubular member may be configured to have an open window at its distal end. In such embodiments, the outer tubular member may be configured to completely cover the open window area of the intermediary tubular member for safe insertion of the medical device.

In all the above embodiments, it should be understood that the connections, the sealing, and securing between the outer tubular member, the inner tubular member, the cannulated armature, the cannulated plunger, the cannulated shaft, and the motor assembly may be achieved through the necessary supporting bearings, connectors, couplers, springs, and other means known in the art. It should also be understood that the connections, the sealing, and securing between other components such as nosecone may be similarly achieved.

In another aspect, the present disclosure provides a method of making a medical device as described herein. In an embodiment, the method includes making a medical device with a first electrode disposed at the distal end of the tubular member as described herein. In an embodiment, the present disclosure also provides a method of making a medical device with a first electrode and a second electrode disposed at the distal end of the tubular member as described herein. In an embodiment, the method includes making a medical device as described herein by using a microfabrication process. In an embodiment, the method includes making a medical device as described herein by employing a flexible circuit process. In an embodiment, the method includes making a medical device as described herein by employing a conductive ink process.

In the above embodiments, the first electrode and the second electrode are configured to provide RF energy to perform cutting and/or coagulation for a medical device as described herein. The first electrode may be formed by insulating part of the distal end of a metallic outer tubular member such as stainless steel outer tubular member while the second electrode may be made on a dielectric insulation layer through microfabrication process, or flexible circuit process, or conductive ink process. For example, the dielectric insulation layer may be deposited on a metallic tubular member through physical vapor deposition, or spray coating or injection molding, or heat shrinking, or dip coating or powder coating. Then, a conductive layer may be applied to the dielectric insulation layer through physical vapor deposition or conductive inking. Finally, another optional insulation layer may be applied to the conductive layer through a process similar to that described for the formation of the dielectric insulation layer such as physical vapor deposition, or spray coating or injection molding, or heat shrinking, or dip coating or powder coating. The dielectric materials may be any suitable materials such as $SiO_2$, $Al_2O_3$, parylene, ceramic, liquid silicone rubber, nylon, polydimethylsiloxane (PDMS), polyimide, polyamide, polyester and other polymeric materials. The conductive materials may be aluminum, stainless steel, silver, gold, titanium, copper, and solder. The additional insulation layer may be materials such as $SiO_2$, $Al_2O_3$, parylene, ceramic, liquid silicone rubber, nylon, polydimethylsiloxane, Halas and Epoxy. The dielectric insulation layer or the additional insulation layer may be at a thickness of from about 0.001" to about 0.01", preferably, from about 0.001" to about 0.003". The conductive layer may be at a thickness of about 0.001" to about 0.01", preferably, from about 0.001" to about 0.002". The preferred conductive material may be gold.

In the above embodiments when the electrical function of the first electrode is from the metallic outer tubular member and the electrical function of the second electrode is from the conductive layer disposed on an insulation layer, the open window and its neighbouring areas at the distal end of the outer tubular member is kept intact to be used as the first electrode. A dielectric layer is then placed around the outer surface of the outer tubular member. The second electrode is subsequently formed by placing a conductive layer over a dielectric layer. This conductive layer is configured to have a runner which is configured to be connectable to a metallic wire. It should be understood that it is preferable to have similar overall cross-sectional areas for each of the two electrodes because this helps ensure proper current density across tissues. It should also be understood that it may be preferable to maintain a consistent insulation gap between the electrodes. For example, this gap may be optimized at approximately 0.030" because this distance allows for proper tissue effect when a proper generator setting is used. It should further be understood that placing the electrodes as close to the cutting window has advantages for a surgeon because it allows the surgeon to control bleeding without having to re-orient the device.

In some embodiments, both the first electrode and the second electrode may be formed from conductive layers disposed on a polymeric outer tubular member through a method such as disclosed in the U.S. Pat. No. 9,289,141, the contents of which are incorporated herein in its entirety by reference. More particularly, both the first electrode and the second electrode may be made to have a head portion and a tail portion or runner. The runner may be preferably run along the longitudinal direction. The head portion of the first of the two electrodes may be configured to cover the open window and its neighboring areas of the outer tubular member. The head portion of the other electrode may then be configured to surround the first electrode to the extent that it does not interfere with the runner of the first electrode. The gap between the two head portions is preferably configured to remain constant, for example, at about 0.02" to 0.030". The head portion is the major conductive area while the runner is a narrower portion that is used to extend between the electrode head and the point where the runner terminates and is attached to a bundle of sheath of external wires. Even though a runner may be disposed in any manner, it is preferably disposed on the outer surface of the outer tubular member along its longitudinal axis direction. In the above embodiments, there is no need for an additional insulation layer between the first electrode and the second electrode since the outer tubular member itself is made of non-conductive polymeric material. Both of the conductive layers may be made through a method as described herein and in the U.S. Pat. No. 9,289,141.

In the above embodiments, the medical device may be configured for use as a microdebrider or shaver in the removal of nasal polyps, sub-mucosal debulk of turbinate, and functional endoscopic sinus surgery (FESS), primarily in the office environment and/or cost-sensitive regions. It may be a disposable debrider or shaver. In the above embodiments, the medical device may provide several benefits such as more precise cutting, lower blood loss or less bleeding in comparison with a conventional medical device without a bipolar design as described herein In another embodiment, the present disclosure also provides a method of cutting tissue. In an embodiment, the method includes providing a medical device having an inner tubular member and an outer tubular member. In an embodiment, the method includes inserting the medical device into a treatment site and positioning the medical device properly. In an embodiment, the method includes turning on the device to cut tissue. More particularly, the method includes cutting tissue by reciprocating or oscillating and/or translating the inner tubular member in relation to the outer tubular member wherein the outer tubular member and the inner tubular member work to admit and cut tissue. It should be understood that once the medical device is turned on, the open window of the outer tubular member constantly aligns with the open distal end of the inner tubular member to capture/admit and cut the tissue. It should also be understood that once the device is powered off, the distal end of the inner tubular member and the distal end of the outer tubular member may be configured to form a closed configuration to keep the device safe for the patient. In an embodiment, the present disclosure also provides a method of cutting tissue and coagulating following the cutting.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

The principles of the present disclosure may be better understood with reference to the drawings and the accompanying descriptions, wherein like reference numerals have been used throughout to designate identical or similar elements. It should be understood that these drawings are not necessarily are drawn to scale. They are presented just for illustrative purposes only, and are not intended to limit the scope of the disclosure. Examples of materials, dimensions, and constructions are included for some elements. Those of ordinary skill in the art should understand that many of the examples provided have suitable alternatives and these alternatives should also be considered within the scope of this disclosure. Moreover, certain terminology is used herein for convenience only and is not to be taken as a limitation on the present disclosure.

The explanations and illustrations presented herein are intended to acquaint others skilled in the art with the disclosure, its principles, and its practical applications. Those skilled in the art may adapt and apply the disclosure in numerous forms, as may be best suited to the requirements of a particular use. The specific embodiments of the present disclosure as set forth are not intended to be exhaustive or limiting of the invention. The scope of the invention should be determined not with reference to the above description, but should be determined with reference to the appended claims, along with the full scope of equivalents to which such claims are entitled.

The terms "one embodiment", "an embodiment", "another embodiment", "some embodiments", "other embodiments", "above embodiment", and similar expressions indicate that the embodiment or embodiments described may include a particular feature, structure, or characteristic, but every embodiment may not necessarily include the particular feature, structure, or characteristic. Moreover, such phrases are not necessarily referring to the same embodiment. Furthermore, when a particular feature, structure, or characteristic is described in connection with an embodiment, it would be within the knowledge of one skilled in the art to incorporate such feature, structure, or characteristic into other embodiments, whether or not explicitly described, unless clearly stated to the contrary. That is, the various individual elements described below, even if not explicitly shown in a particular combination, are nevertheless contemplated as being combinable with each other to form other additional embodiments or to complement and/or enrich the described embodiment or embodiments, as would be understood by one of ordinary skill in the art.

The articles "a", "an" and "the" are used herein to refer to one or to more than one (i.e. to at least one) of the grammatical object of the article unless otherwise clearly indicated by contrast. By way of example, "an element" means one element or more than one element.

The term "including" is used herein to mean, and is used interchangeably with, the phrase "including but not limited to". The term "or" is used herein to mean, and is used interchangeably with, the term "and/or", unless context clearly indicates otherwise.

The term "such as" is used herein to mean, and is used interchangeably, with the phrase "such as but not limited to". Unless specifically stated or obvious from context, as used herein, the term "about" is understood as within a range of normal acceptance in the art, for example within standard deviations of the mean.

The term "proximal" is herein used to mean a position or direction closest to a user of the device and is in a position or direction opposite to the term "distal".

The term "distal" is herein used to mean a position or direction furthest away from a user of the device and is a position or direction opposite to the term "proximal".

The term "cannulated" used throughout the specification refers to a general 'tube' or 'tubular', or 'hollowed out cylindrical' shape, or any general cylinder shape having an outside diameter and an inside diameter, for example.

All numeric values are herein assumed to be modified by the term "about" whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. Even more specifically, "about" can be understood as within 10%, 9%, 8%, 7%, 6%, 5%, 4%, 3%, 2%, 1%, 0.5%, 0.1%, 0.05%, or 0.01% of the stated value. Unless otherwise stated, all ranges include both endpoints and all numbers between the endpoints. The use of "about" or "approximately" in connection with a range applies to both ends of the range. Thus, "about 10 to 30" is intended to cover "about 10 to about 30", inclusive of at least the specified endpoints.

What is claimed is:

1. A medical device comprising:
 a tubular member extending along a longitudinal axis from a proximal end to a distal end, the tubular member including an open window disposed at the distal end;

a first electrode disposed at the distal end of the tubular member, wherein the first electrode surrounds the open window of the tubular member or its neighboring region;

an insulation zone surrounding the first electrode; and a second electrode including a head portion surrounding the insulation zone and a runner that extends proximally on an outer surface of the tubular member toward the proximal end of the tubular member in a direction substantially parallel to the longitudinal axis, wherein the head portion bifurcates from the runner at a location proximal to the open window.

2. The medical device of claim 1, wherein the open window of the tubular member is configured to be substantially symmetrical along a longitudinal axis of the tubular member.

3. The medical device of claim 2, wherein the first electrode is substantially symmetrical along the longitudinal axis of the tubular member.

4. The medical device of claim 2, wherein the first electrode is asymmetrical along the longitudinal axis of the tubular member.

5. The medical device of claim 2, wherein the second electrode is substantially symmetrical along the longitudinal axis of the tubular member.

6. The medical device of claim 2, wherein the second electrode is asymmetrical along the longitudinal axis of the tubular member.

7. The medical device of claim 1, wherein the medical device further comprises an inner tubular member configured to be received within the tubular member.

8. The medical device of claim 7, wherein the inner tubular member is configured to have an open distal end.

9. The medical device of claim 8, wherein the open distal end of the inner tubular member and the open window of the tubular member are configured to form a cutting tool during an operation of the medical device.

10. The medical device of claim 7, wherein the inner tubular member is configured to have a distal end and an open window disposed at the distal end.

11. The medical device of claim 7, wherein the medical device further comprises a cannulated armature configured to be operably connected to the inner tubular member.

12. The medical device of claim 1, wherein the head portion of the second electrode surrounds the insulation zone by connecting bifurcated segments of the second electrode at a location distal to the open window.

13. A medical device comprising:

an outer tubular member extending along a longitudinal axis from a proximal end to a distal end, the outer tubular member including an open window disposed at the distal end;

an inner tubular member having a distal end and an open window disposed at the distal end;

a cannulated armature configured to drive the inner tubular member;

a first electrode disposed at the distal end of the outer tubular member and surrounding the open window of the outer tubular member or a neighboring region of the open window;

an insulation zone surrounding the first electrode; and a second electrode including a head portion surrounding the insulation zone and the first electrode such that the insulation zone is bounded by the first electrode along an inner perimeter of the insulation zone and by the second electrode along an outer perimeter of the insulation zone, the second electrode further including a runner that extends proximally on an outer surface of the outer tubular member toward the proximal end of the outer tubular member in a direction substantially parallel to the longitudinal axis, the head portion bifurcating from the runner at a location proximal to the open window;

wherein a longitudinal length of the insulation zone on a top side of the outer tubular member along the longitudinal axis is greater than a longitudinal length of the head portion of the second electrode on the top side of the outer tubular member along the longitudinal axis.

14. The medical device of claim 13, wherein the open window of the outer tubular member is configured to be substantially symmetrical along the longitudinal axis of the outer tubular member.

15. The medical device of claim 13, wherein the first electrode is substantially symmetrical along the longitudinal axis of the outer tubular member.

16. The medical device of claim 13, wherein the first electrode is asymmetrical along the longitudinal axis of the outer tubular member.

17. The medical device of claim 13, wherein the second electrode is substantially symmetrical along the longitudinal axis of the outer tubular member.

18. The medical device of claim 13, wherein the second electrode is asymmetrical along the longitudinal axis of the outer tubular member.

19. A medical device comprising:

a tubular member extending along a longitudinal axis from a proximal end to a distal end, the tubular member including an open window disposed at the distal end;

a first electrode disposed at the distal end of the tubular member;

an insulation zone disposed at the distal end of the tubular member; and a second electrode disposed at the distal end of the tubular member, the second electrode including a head portion and a runner, the runner extending proximally on an outer surface of the tubular member toward the proximal end of the tubular member in a direction substantially parallel to the longitudinal axis;

wherein the first electrode encompasses the open window of the tubular member, the insulation zone encompasses the first electrode, and the head portion of the second electrode encompasses the insulation zone and the first electrode such that the insulation zone is bounded by the first electrode along an inner perimeter of the insulation zone and by the second electrode along an outer perimeter of the insulation zone;

wherein the head portion of the second electrode bifurcates from the runner at a location proximal to the open window; and wherein a longitudinal length of the insulation zone on a top side of the tubular member along the longitudinal axis is greater than a longitudinal length of the head portion of the second electrode on the top side of the tubular member along the longitudinal axis.

* * * * *